(12) United States Patent
Robinson (10) Patent No.: US 8,029,514 B2
(45) Date of Patent: Oct. 4, 2011

(54) BONE SCREW REMOVAL SYSTEM

(76) Inventor: James C. Robinson, Atlanta, GA (US)

( * ) Notice: Subject to any disclaimer, the term of this patent is extended or adjusted under 35 U.S.C. 154(b) by 410 days.

(21) Appl. No.: 12/309,985

(22) PCT Filed: Aug. 6, 2007

(86) PCT No.: PCT/US2007/017445
§ 371 (c)(1),
(2), (4) Date: Apr. 21, 2009

(87) PCT Pub. No.: WO2008/019119
PCT Pub. Date: Feb. 14, 2008

(65) Prior Publication Data
US 2009/0318932 A1    Dec. 24, 2009

Related U.S. Application Data

(60) Provisional application No. 60/821,456, filed on Aug. 4, 2006.

(51) Int. Cl.
*A61B 17/88* (2006.01)

(52) U.S. Cl. ........................................................ 606/104

(58) Field of Classification Search .................. 606/280, 606/286, 289, 290, 294, 295, 301, 96, 99, 606/104, 86 B; 81/448, 451, 452; 7/165; D08/82
See application file for complete search history.

(56) References Cited

U.S. PATENT DOCUMENTS

| | | | | |
|---|---|---|---|---|
| 5,354,302 A | * | 10/1994 | Ko | 606/104 |
| 6,331,179 B1 | * | 12/2001 | Freid et al. | 606/279 |
| 2006/0074418 A1 | * | 4/2006 | Jackson | 606/61 |

* cited by examiner

*Primary Examiner* — Eduardo C Robert
*Assistant Examiner* — David Comstock
(74) *Attorney, Agent, or Firm* — FSB FisherBroyles, LLP; Anthony J DoVale (57) ABSTRACT

A bone screw removal system for a bone screw retaining system that includes an implant having a plate, which defines a plurality of transversely extending bores that are configured to receive a bone screw for engaging the plate to the cervical spine, and an elastically deformable spring member positioned therein a cavity of the plate such that portions of the spring member can extend into a portion of an upper region of each of the bores of a pair of opposing bores, the spring member being movable between a first relaxed, expanded position and a second, compressed position. The bone screw removal system having at least one tongue member that is configured to selectively act on the spring member of the bone screw retaining system.

19 Claims, 6 Drawing Sheets

BONE SCREW REMOVAL SYSTEM

CROSS-REFERENCE TO RELATED APPLICATION

This application claims priority to and the benefit of U.S. Provisional Application No. 60/821,456, filed Aug. 4, 2006, which is incorporated in its entirety in this document by reference.

FIELD OF THE INVENTION

The present invention relates generally to surgical procedures, most particularly for use in fixation of the cervical spine. More particularly, the invention pertains to a bone screw removal system for use in removing screws from a plate system, such as, for example, those for use in anteriorly fixating adjacent cervical vertebrae.

BACKGROUND OF THE INVENTION

As with any bony structure, the spine is subject to various pathologies that compromise its load bearing and support capabilities. The spine is subject to degenerative diseases, the effects of tumors and, of course, fractures and dislocations attributable to physical trauma. In the past, spinal surgeons have tackled the thorny problems associated with addressing and correcting these pathologies using a wide variety of instrumentation and a broad range of surgical techniques. For example, in spinal surgeries, the fusion of two or more vertebral bodies is required to secure a portion of the spinal column in a desired position. Alternatively, the use of elongated rigid plates has been helpful in the stabilization and fixation of the lower spine, most particularly the thoracic and lumbar spine.

The cervical spine can be approached either anteriorly or posteriorly, depending upon the spinal disorder or pathology to be treated. Many of the well known surgical exposure and fusion techniques of the cervical spine are described in *Spinal Instrumentation*, edited by Drs. Howard An and Jerome Cotler. This text also describes instrumentation that has been developed in recent years for application to the cervical spine, most frequently from an anterior approach.

The anterior approach to achieving fusion of the cervical spine has become the most popular approach. During the early years of cervical spine fusion, the fusions were preformed without internal instrumentation, relying instead upon external corrective measures such as prolonged recumbent traction, the use of halo devices or minerva casts, or other external stabilization. However, with the advent of the elongated plate customized for use in the cervical spine, plating systems have become the desired internal stabilization device when performing stabilization operations.

It has been found that many plate designs allow for a uni-corticaly or bi-corticaly intrinsically stable implant. It has also been found that fixation plates can be useful in stabilizing the upper or lower cervical spine in traumatic, degenerative, tumorous or infectious processes. Moreover, these plates provide the additional benefit of allowing simultaneous neural decompression with immediate stability.

During the many years of development of cervical plating systems, particularly for the anterior approach, various needs for such a system have been recognized. For instance, the screws used to connect the plate to the vertebrae must not loosen over time or back out from the plate. This requirement, that the bone screws do not loosen over time or back out from the plated, tends to complicate implantation of known plating systems. Such bone screw retention systems generally ensure that the bone screws placed into the vertebrae through the plating system do not back out voluntarily from the plate, but typically do not adequately permit the removal of an associated bone screw when desired by the surgeon.

It remains desirable in the pertinent art to provide a bone screw removal system for use with a plating system that addresses the limitations associated with known systems, including but not limited to those limitations discussed above.

SUMMARY

In one embodiment of the present invention, a bone screw removal system comprises a driver assembly that is configured to drive bone screws used to fixate a plate system having a bone screw retention system and is further configured to remove screws therefrom the plate system.

Related methods of operation are also provided. Other systems, methods, features, and advantages of the bone screw removal system will be or become apparent to one with skill in the art upon examination of the following figures and detailed description. It is intended that all such additional systems, methods, features, and advantages be included within this description, be within the scope of the bone screw removal system, and be protected by the accompanying claims.

DETAILED DESCRIPTION OF THE FIGURES

The accompanying drawings, which are incorporated in and constitute apart of this specification, illustrate certain aspects of the instant invention and together with the description, serve to explain, without limitation, the principles of the invention.

DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. Those skilled in the relevant art will recognize that many changes can be made to the embodiments described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "bore" includes aspects having two or more bores unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

In one embodiment, and referring to FIGS. 1-4A, a plate system for use with the present invention can comprise an implant 10, particularly for the spinal column, that can have a joining member 20 such as a plate 22 that defines a plurality of openings or bores 24, bone screws 50 capable of being accommodated in the bores, and at least one spring member 70 configured for releasably securing the bone screws therein the bores. In one aspect, the spring member can come into direct contact with the bone screw to secure the bone screw within the bores. Optionally, the spring member can form a blocking element to secure the bone screw within the bores. Further, the bone screw removal system of the present invention provides for the selective removal of the bone screw or screws from the plate at the physicians desire.

Figure 1:
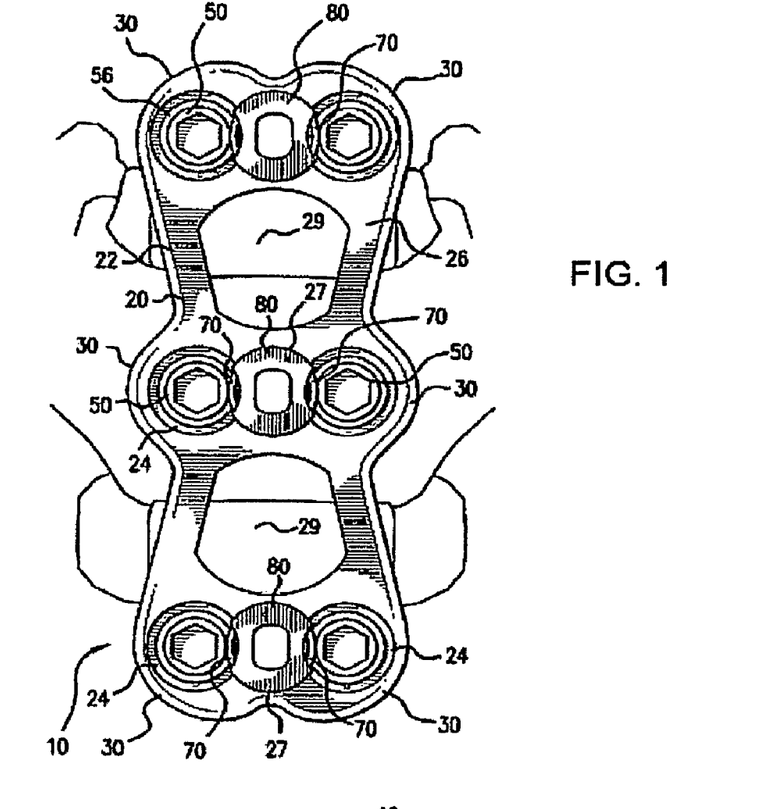
FIG. 1 is a top plan view of an exemplary bone screw retention system comprising a plate having a plurality of bores therein and a plurality of spring members shown in a locking position with a plurality of seated bone screws.
Figure 2:
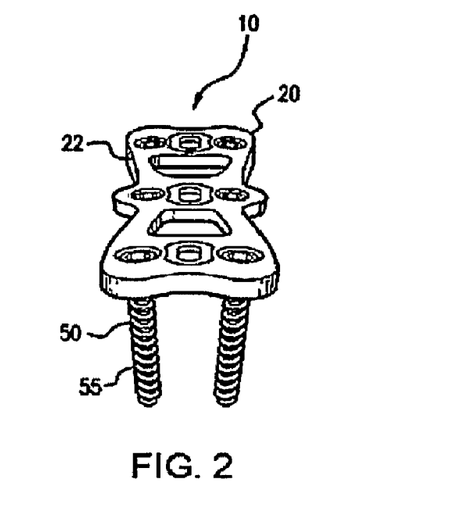
FIG. 2 is a perspective view of the bone screw retention system of FIG. 1, showing a plurality of bone screws seated therein the bores of the plate and positioned at desired angles relative to the plate.
Figure 3:
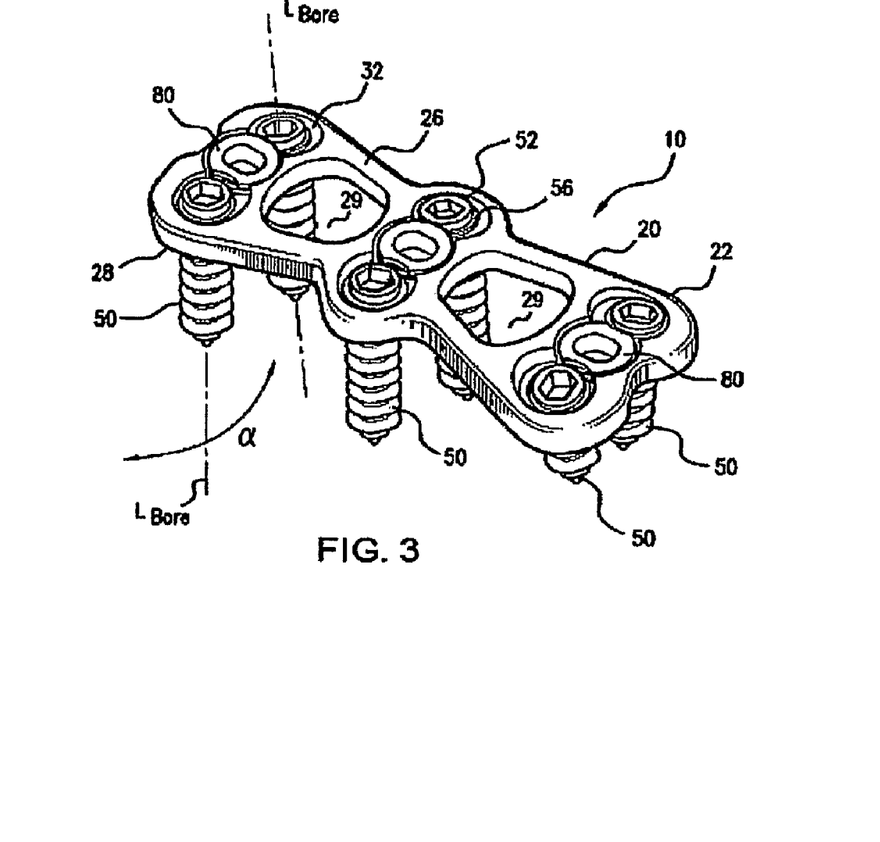
FIG. 3 is a perspective view of the plate of the bone screw retention system of FIG. 1, showing a spring member comprising a split-ring operable mounted in a spring mount such that, in a first relaxed position, a portion of the split-ring extends over a portion of the upper region of the bore.

In one aspect, the joining member 20 comprises a plate 22 that defines a plurality of transversely extending bores 24 that are counter sunk a predetermined distance. In one exemplary aspect, a head 52 of a bone screw 50 can be configured to be posteriorly displaceable through a bore 24 of the plate from an anterior surface 26 to a posterior surface 28 of the plate and retained within a portion of the bore between the posterior and anterior surfaces 26, 28. In one aspect, the plate 22 can have a generally elongated form whose outline generally departs from rectangular due to the presences of partial lobes 30 or lateral projections at the corners and at the center of the sides of the plate. Each partial lobe 30 has a rounded outline and, in an exemplary aspect, can define one respective bore 24. It is, of course, contemplated that other shapes of the plate may be employed.

As noted above, the plate defines a plurality of bores 24 that extend substantially transverse therethrough the plate between the anterior and posterior surfaces 26, 28 of the plate and that are configured for operable receipt of the bone screw or bone anchor. In one aspect, the bores 24 extend along a longitudinal axis from the anterior surface to the bottom bone contacting posterior surface of the plate. In one aspect, each bore 24 has an upper region 32 with a first diameter and a lower region 34 that includes a seat 36 for the bone screw and a posteriorly extending tubular shaft 38 that extends to an opening on the posterior surface 28 of the plate 22. In one aspect, the seat 36 of the bore can have at least a partial spherical shape. In another aspect, the bores comprise a plurality of paired opposing bores In a further aspect, the bone screw 50 has a head 52 with a maximum diameter that is smaller than the first diameter of the upper region 32 of the bore, which thereby allows the screw head to pass through that region of the bore. In one example, the bone screw can be a conventional self-tapping bone screw. It is of course contemplated that conventional non self-tapping bones screws can be used with the system of the present invention. Further, it is contemplated that conventional bone screws with at least partially rotatable heads can be used if a semi-rigid fixation procedure is desired.

In various exemplary aspects, the head 52 of each bone screw 50 can comprise a complementary tapered section 51 that extends outwardly therefrom the threaded shank portion 54 of the bone screw. In this aspect, the tapered section 51 can have a tapered surface 53 that extends from a shank 55 of the bone screw toward an upwardly facing shoulder surface 56 of the bone screw which is formed by a portion of the shoulder 57 of the head of the bone screw. A portion of the bone screw above the upwardly facing shoulder surface 56 of the bone screw is conventionally configured for operative engagement with a driving tool 2 and has a reduced diameter relative to the diameter of the shoulder of the head of the bone screw.

In one aspect, the seat 36 is configured for complementary receipt of the shank 55 of the bone screw 50 such that the bone screw can be fixed at a predetermined angle with respect to the plate. Alternatively, the bone screw can be fixed at an operator selective angle, i.e., be angularly displaceable. In one example, the tapered section 51 of the bone screw can be configured for complementary rotatable contact with an exemplary spherically shaped seat of the bore. It is contemplated that the tapered section 51 of the bone screw can be substantially linear or, optionally, substantially spherical. Further, the shank 55 of the bone screw can be threaded in any well known fashion and may include an axial groove to enable the bone screw to be self-boring and self-tapping.

In another aspect, the shaft 38 of the bore can have an operative diameter that is greater than the diameter of the shank 55 of the bone screw intermediate the head of the bone screw and its distal end. As a result, the bone screw 50 is angularly displaceable within the shaft of the bore between the seat and the posterior surface opening. The bone screw can thus be tilted within the shaft 38 of the bore relative to the longitudinal axis of the bore to facilitate positioning the bone screw 50 at a desired location in the bone by advancing the threaded shank portion 54 of the bone screw within the bone at an angle relative to the posterior surface of the plate. In one aspect, the bone screw 50 can be angularly displaced relative to the longitudinal axis of the bore up to an angle α of about 20 degrees. Thus, the surgeon has, at his disposal, the freedom to orient the bone screw angularly with respect to the joining member or plate, which allows him to optimize the anchorage. In one aspect, the bone screws can be rotatably mounted therein the underlying bone tissue using a conventional screw driver, a drive socket, and the like.

In one embodiment of the present invention, the spring member 70 comprises a circlip 72. In one exemplary aspect, the circlip 72 is in the form of a circular split-ring 74 having spaced opposed ends. In one embodiment, at least portions of one circlip is common to two bores 24 in the plate 22, for example, the two bores 24 forming a pair of opposing bores. In an alternative embodiment, at least a portion of one respective circlip is common to one individual bore 24 of the plate 22. As used herein, the terms "circlip" and "split-ring" are used interchangeably without intended limitation. As described herein, it is contemplated that the exemplified plate, bone screws and split-rings may be supplied as part of a bone screw retaining system for use by a surgeon.

In one embodiment, the plate 22 further defines a plurality of cavities 27. In one exemplary aspect, at least a portion of the cavity 27 forms a transversely extending cavity that opens on both the posterior and anterior surfaces of the plate. In another aspect, the plurality of cavities can be spaced substantially along the longitudinal axis of the plate 22. In a further aspect, one cavity 27 is positioned therebetween each pair of bores 24. In this aspect, it is contemplated that the cavity can be positioned adjacent to and equidistant from each bore of the respective pair of bores.

In another aspect, one spring member 70, e.g., one split-ring 72, is operable positioned therein each cavity 27 such that portions of the spring member can extend into a portion of the upper region of each of the bores of the paired opposing bores. In this aspect, the elastically deformable spring member 70 is configured to mount therein the cavity 27 and is movable between a first relaxed, expanded position and a second, compressed position. In one aspect, the spring member 70 is mounted to extend outwardly substantially transverse to the longitudinal axis of the bore and into the upper region of the bore. As one will appreciate, in the second position, the spring member 70 has a diameter that is less than the diameter of the spring member when it is in the first, relaxed position. Further, in this aspect, when the spring member 70 is in the first relaxed position, portions of the spring member extend over portions of the upper region 32 of each bore of the paired opposing bores, which decreases the effective inner diameter of the upper region 32 of the bore. In another aspect, when the spring member 70 is in the second, compressed position, portions of the spring member 70 are medially biased away from the longitudinal axis of the bore 24 toward the diameter of the outer wall of upper region 32 of the bore. As one will appreciate, the effective inner diameter of the upper region 32 of the bore is thereby increased when the spring member 70 is in the second position.

Figure 4A:
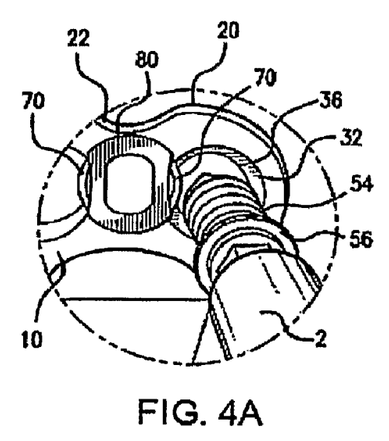
FIG. 4A is a perspective view of a bone screw being initially placed therein the bore of the plate.
Figure 4B:
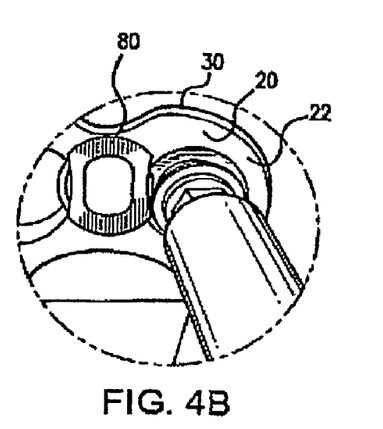
FIG. 4B is a perspective view of the bone screw being advanced into the underlying bone, showing the spring member being deflected medially by the taper of the head of the bone screw which allows it to pass by the spring member.
Figure 4C:
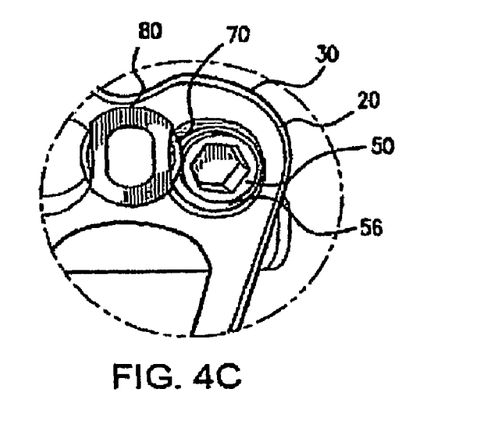
FIG. 4C is a perspective view of the bone screw as it is advances sufficiently past the spring member such that the spring member biases back to its original relaxed position in which at least a portion is a perspective view of a bone screw being initially placed therein the bore of the plate of the spring member overlies a portion of the now underlying bone screw.

In one exemplified embodiment of the present invention, and as shown in FIGS. 4A-4C, the split-ring 74 is mounted therein the cavity 27 and the bone screw is inserted therein the bore of the plate (shank first into the plate from the anterior surface of the plate) and is advanced posteriorly within the bore 24. The tapered section 51 of the head 52 of the bone screw engages the split-ring and applies a radially expanding force against a peripheral surface of the split-ring to forcefully move the split-ring medially from the first position toward the second, compressed position. One would appreciate that the interaction between the split-ring 74 and the head 52 of the bone screw causes the effective inner diameter of the upper region 32 of the bore to increase to a size that allows for the posterior passage of the head of the bone screw past the split-ring. In this aspect, after the shoulder 57 of the head of the bone screw passes the operative plane of the spring member, the split-ring biases medially back to its first relaxed position such that a portion of the split-ring overlies a portion of the upwardly facing shoulder surface 56 of the head of the bone screw. Thus, when the split-ring 74 relaxes to its unexpanded state, it prevents the bone screw 50 from backing out of the plate as the effective inner diameter of the upper region 32 of the bore is less than the diameter of the head of the bone screw, which effectively blocks the path that the bone screw would have to traverse to back out or exit the bore in the plate. With the bone screw 50 positioned against the seat 36 of the bore, the distal threaded portion of the bone screw is embedded in, and secured to, the bone of the patient.

In one aspect, when the head 52 of the bone screw fully engages the seat 36 of the plate, the upwardly facing shoulder surface 56 of the bone screw is located at or below the substantially transverse plane of the spring member 70. In this position, as one will appreciate, the spring member biases back toward and/or to its relaxed position because the portion of the bone screw above the plane of the spring member has a reduced diameter relative to the upwardly facing surface portion of the bone screw.

In one aspect, the system of the present invention further comprises a spring mount 80 adapted to fixedly mount therein the cavity. In a further aspect, the spring mount is configured for a compressive fit within the cavity 27. In another aspect, a portion of opposing side walls 82 of the spring mount is recessed such that the upper region of the bore and the recessed edge portion 84 of the spring mount define a generally circular countersunk well 85 that is sized to receive the bone screw. In the relaxed position, a portion of the spring member 70, 74 spans across a portion of the recessed edge portion 84 and extends outwardly over a portion of the countersunk well substantially transverse to the longitudinal axis of the bore. In one aspect, the spring mount 80 has a groove 86 and/or slot defined therein the side walls of the spring mount, which is configured to receive a portion of the spring member 70 as it is medially biased toward its second, compressed position when the bone screw is being inserted therein the bore of the plate. In a further aspect, the opposed ends of the spring clip can be enclosed therein the spring member.

In one embodiment, the spring member is formed from a biocompatible, flexible material such as, and not meant to be limiting, titanium alloy and the like as disclosed in U.S. Pat. Nos. 4,857,269 and 4,952,236, which are incorporated in their entirety herein by reference. Further, polymeric materials such as, for example, ultra-high molecular weight polyethylene can also be used to form the spring member of the present invention.

In another aspect, the plate can define a pair of opposing openings 29. In this aspect, the pair of openings 29 is generally positioned on the longitudinal axis of the plate. In a further aspect, each opening 29 is positioned intermediate the center and an end of the plate. Thus, in an embodiment having bores 24 in each of the partial lobes at the corners of the end of the plate and in the partial lobes at the center of the plate; it is contemplated that the opening can be positioned substantially between the respective bores. Thus, in this aspect, the plate forms a substantially open frame. These opposed openings 29 allow for visualization of the underlying bone and tissue as the implant is being fixated.

In one aspect, the plate 22 may be curved to match the anatomical curvatures. Thus, the implant curved to best suit the anatomy and natural curvature of the spinal column in the case of a spinal application. Of course, the plate 22 may be used in fracture fixation, as a tibial base plate, as a hip side plate or any application where bone plates and screws are used. For these uses, a larger screw than that described herein is necessary. Thus, it is contemplated that the screw locking system of the present invention can be scaled up or down as necessary so that any size screw can be utilized.

Figure 5:
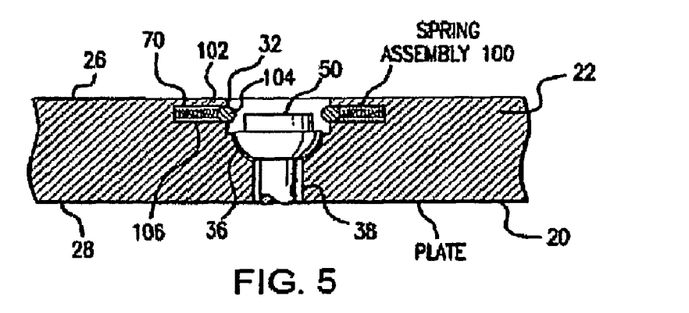
FIG. 5 is a partial cross-sectional view of an alternative embodiment of the bone screw retention system showing a plurality of spring members mounted therein the upper portion of each bore of the plate; each spring member comprising a spring assembly that comprises a movable piston member biased by a coil spring.
Figure 6:
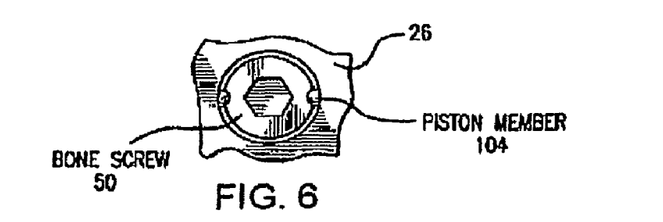
FIG. 6 is a partial top plan view of the bone screw retention system of FIG. 5.

Referring to FIGS. 5 and 6, in another embodiment, the bone screw retention system of the plate system can comprise a spring member 70. In this aspect, the spring member can comprise at least one spring member 100 that comprises a coil spring 102 and a piston member 104. In this embodiment, the spring member is mounted therein a portion of the bore 24 such that in a relaxed position, a portion of the piston member 104 of the spring member extends over a portion of the upper region of the bore. In this aspect, a portion of the wall of the upper region of the bore defines an orifice 106 that is adapted to moveably receive the coil spring and at least a portion of the piston member therein. As one skilled in the art will appreciate, the piston member 104 is captured therein the orifice 106 such that it can not be ejected from the orifice by the urging of the coil spring. Thus, the coil spring of the spring member is positioned therein a portion of the wall of the upper region 32 of the bore. Of course, it is contemplated that a plurality of spring member can be mounted in each bore of the plate.

In use, upon insertion of the bone screw into the bore of the plate and its subsequent posterior movement, the tapered surface 53 of the head 52 of the bone screw acts on the piston member 104 to force the piston member back into orifice by acting on, i.e., compressing, the underlying coil spring. In one aspect, when the head 52 of the bone screw fully engages the seat 36 of the plate, the upwardly facing shoulder surface of the bone screw is located at or below the plane of the piston member. In this position, as one will appreciate the coil spring 102 acts on the piston member 104 and bias the piston member outwardly toward and/or to its fully extended position.

Figure 7:
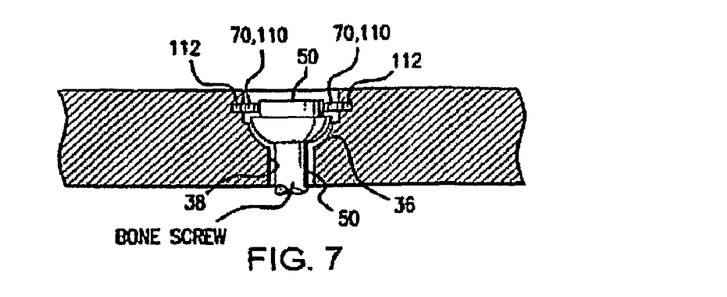
FIG. 7 is a partial cross-sectional view of an alternative embodiment of the bone screw retention system showing at least one spring member mounted therein the upper portion of each bore of the plate; each spring member comprising an arcuate spring member mounted therein the wall of the upper region of the bore and which is shown in its first, relaxed position.
Figure 8:
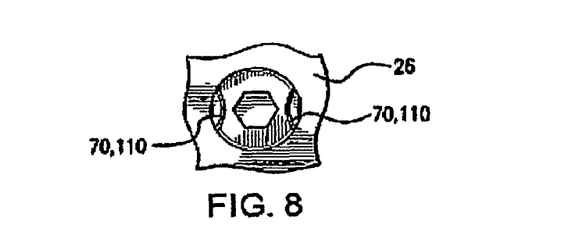
FIG. 8 is a partial top plan view of the bone screw retention system of FIG. 7.

In a further exemplary embodiment of a bone screw retention system, and as shown in FIGS. 7 and 8, the spring member 70 can be at least one arcuate spring member 110 that is mounted to a portion of the upper region 32 of the bore such that in a relaxed position, a portion of the arcuate spring member 110 extends over a portion of the upper region of the bore substantially transverse to the longitudinal axis of the bore. A portion of the wall of the upper region of the bore can define a groove 112 and/or slot that is adapted to receive a portion of the arcuate spring member 70 as it is biased toward its second, compressed position when the bone screw is being inserted therein the bore of the plate. In a further aspect, the respective ends of the arcuate spring member 110 are mounted therein a portion of the wall of the upper region of the bore. Of course, it is contemplated that a plurality of arcuate spring members can be mounted in each bore of the plate.

Similar to the embodiment described above, in use, upon insertion of the bone screw into the bore 24 of the plate and it subsequent posterior advancement, the tapered surface of the head of the screw 50 acts on the arcuate spring member 110 to force the arcuate spring member toward its second, compressed position. In one aspect, when the head of the bone screw fully engages the seat 36 of the plate, the upwardly facing surface of the bone screw is located at or below the plane of the spring member 70. In this position, as one will appreciate, the arcuate spring member 110 biases toward and/or to its relaxed position because the portion of the bone screw above the plane of the spring member has a reduced diameter relative to the upwardly facing shoulder surface portion of the bone screw.

An exemplary embodiment of the bone screw removal system of the present invention is shown in FIGS. 9-15. In one embodiment, a bone screw removal assembly 230 is shown that comprises an elongated bone screw drive member 240 and a tubular sleeve member 250. In one aspect, the screw drive member has a distal end 242 that is configured to operatively engage the head 52 of a bone screw. In another aspect, the sleeve member 250 is configured to move longitudinally relative to and about the elongate bone screw drive member. Of course, it is contemplated that that the sleeve member can be slidably mounted thereto the bone screw drive member.

Figure 9:
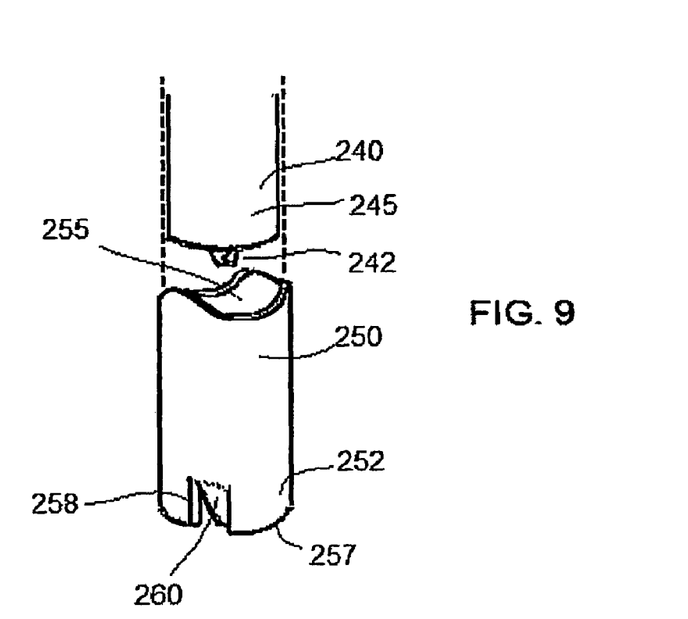
FIG. 9 is a partial perspective view of a screw removal assembly shown in a first position in which a distal end portion of a bone screw drive member is positioned within, and at least partially enclosed by, the distal end of a tubular sleeve member, the distal end of the sleeve member having a tongue member resiliently biased inward toward the center of the sleeve member that is configured to fit over the spring member of an exemplary bone screw retention system in its first, relaxed, position.
Figure 10:
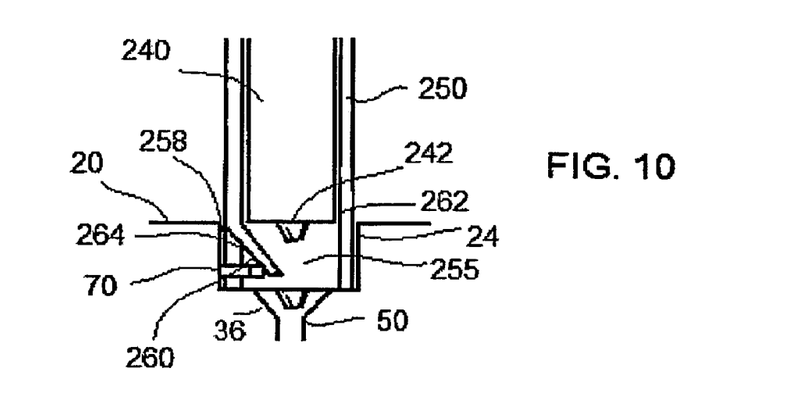
FIG. 10 is a partial fragmentary cross-sectional view of the screw removal assembly of FIG. 9, showing the sleeve member having a tongue member that is configured such that a portion of the exterior surface of the bone screw drive member can act against an inner surface of the tongue member to force portions of the outer surface of the tongue member to act against and compress the spring member of the exemplary bone screw retention system toward its second, compressed position, wherein the distal end portion of the bone screw drive member is configured to operatively engage a head of a bone screw.

In one embodiment, the sleeve member 250 has at least one tongue member 260 formed in a portion of the distal end 252 of the sleeve member. In one exemplary aspect, each tongue member 260, in a first position, is bent or hinged inwardly toward the longitudinal center axis of conduit 261 of the sleeve member that extends from the distal end 252 to the proximal end 253 of the sleeve member 250. In one aspect, the conduit of the sleeve member has a first diameter. In a further aspect, the first aspect of the conduit of the sleeve member is greater than the diameter of the head of the bone screw.

In another aspect, each tongue member 260 is configured to be resiliently biased toward the peripheral wall portions 257 of the distal end of the sleeve member, i.e., toward an operative position, if sufficient force is applied to an inner surface 262 of the tongue member. In the first position, the at least one tongue member defines at least one slot 258 in the peripheral wall of the distal end 252 of the sleeve member. In one aspect, each slot 258 has a width that is greater than the width of the spring member 70 in its first, relaxed position.

Figure 12:
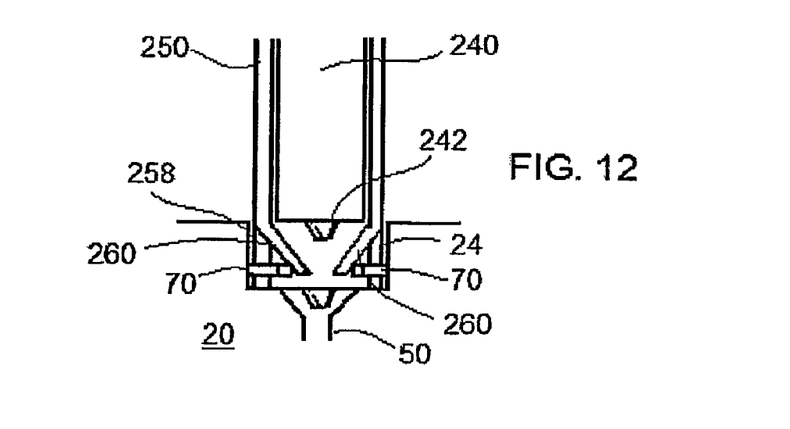
FIG. 12 is a partial fragmentary cross-sectional view of a screw removal assembly, showing the sleeve member having a pair of opposed tongue member that are configured such that a portion of the exterior surface of the bone screw drive member acts against an inner surface of each respective tongue members to force portions of the outer surface of each of the tongue members to act against and compress the spring member of the exemplary bone screw retention system toward its second, compressed position, wherein the distal end portion of the bone screw drive member is configured to operatively engage a head of a bone screw.
Figure 13:
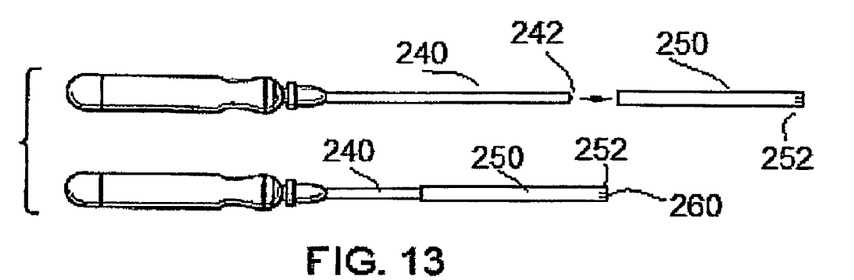
FIG. 13 is a side plan view of an embodiment of the bone screw removal system of the present invention, showing the tubular sleeve member being inserted onto a shaft of the bone screw drive member.

In various exemplary aspects, the at least one tongue member comprises a pair of tongue members or a plurality of tongue members. In another aspect, the at least one tongue member equals the number of spring members of the bone screw retaining system. It is of course contemplated that other designs of the tongue member can be as long as it is resiliently urged to bias as described herein.

Figure 11:
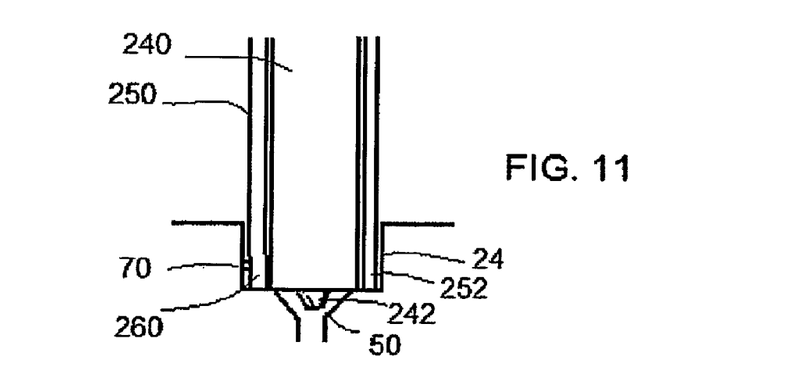
FIG. 11 is a partial fragmentary cross-sectional view of the screw removal assembly of FIG. 9, shown in a second position in which a portion of the exterior surface of the bone screw drive member acts against an inner surface of the tongue member to force portions of the outer surface of each of the tongue members to act against and compress the spring member of the exemplary bone screw retention system toward its second, compressed position, wherein the distal end portion of the bone screw drive member is operatively engaged with the head of the bone screw.
Figure 14:
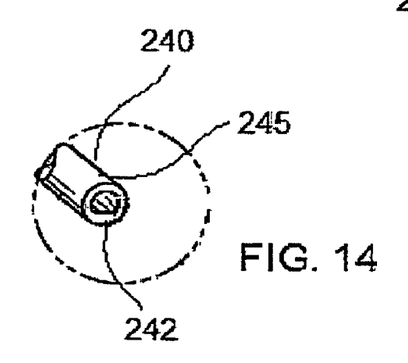
FIG. 14 is an enlarged partial perspective view of the distal end of the bone screw drive member, showing an exterior surface formed at the distal end of the bone screw drive member that is configured to engage the tongue member of the tubular sleeve member.

In use, the sleeve member 250 is placed into a seated position within the bore of the plate such that each respective slot 258 of the sleeve member overlies one respective spring member 70. Thus, each tongue member 260 would be positioned adjacent or in opposition to a spring member 70. The bone screw drive member 240 has an exterior surface 245 that is configured to contact at least a portion of the inner surface 262 of the tongue member such that, as the screw drive member is pushed down into engagement with the head of the bone screw, the exterior surface 245 of the screw drive member 240 acts against the resistance of the tongue member 260 to bias/rotate the tongue member outward toward the peripheral wall 257 of the sleeve member. In this aspect, at least a portion of the exterior surface of the bone screw drive member proximate the distal end of the bone screw member has a diameter that is substantially the same as the first diameter of the sleeve member and is configured for slideable receipt therein the conduit of the sleeve member.

Figure 15:
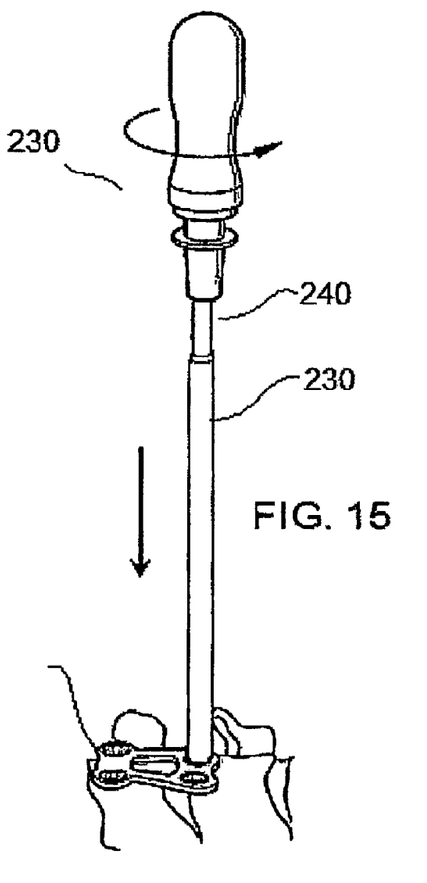
FIG. 15 is a perspective view showing the screw drive member being rotated to back out the bone screw while the distal end of the sleeve member remains in biased contact with the spring elements of the bone screw retaining system.

One would appreciate that, as the tongue member 260 is biased outwardly, the spring member 70, being acted on by the outer surface 264 of the tongue member, moves to its second compressed position. Thereupon, the independent rotation of the screw drive member 240 relative to the sleeve member 250 allows for the removal of the bone screw. When the sleeve member is removed from the bore, the spring member is allowed to bias back to its first relaxed position.

In use, the at least one tongue member is movable about and between a first, relaxed position, and a second, operative position. In the first position, the tongue member is resiliently biased inward toward the center of the conduit 255 of the sleeve member, and, in the second position, the at least a portion of the exterior surface of the bone screw drive member proximate the distal end of the bone screw drive member acts against an inner surface of the at least one tongue member to urge the at least one tongue member outwardly away from the center of the conduit of the sleeve member. The subsequent rotation of the bone screw drive member backs moves both the bone screw and the bone screw drive member in an anterior direction such that the spring member biases back to contact with the tapered portion of the screw as it is anteriorly moved.

In another embodiment, the upper region of the formed bores 24 in the plate 22 have a diameter that is greater than the diameter of the shoulder 57 of the bone screw 50 such that a predetermined spaced is formed between the shoulder of the bone screw and the wall of the upper region 36 of the bore when the bone screw is positioned on the seat of the bore. In this embodiment, the tubular sleeve member is adapted to seat therein the predetermined space such that the removal of the bone screw is not obstructed. In another aspect, the bone screw drive member can be rotated independently of the sleeve member until the bone screw is removed.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

1. A bone screw removal system for removing bone screws from a plate that defines a plurality of transversely extending bores and a plurality of cavities and a bone screw retaining system that includes an elastically deformable spring member positioned therein each cavity such that portions of the spring member can extend into a portion of the upper region of each of the bores, wherein the spring member is configured to mount therein the cavity and is movable between a first relaxed position and a second compressed position, wherein, in the first relaxed position, at least a portion of the spring member extends outwardly substantially transverse to the longitudinal axis of the bore and into the upper region of the bore, wherein, in the first relaxed position, portions of the spring member extend over portions of the upper region of each bore of the pair of opposing bores, which decreases the effective inner diameter of the upper region of the bore, and wherein, in the second compressed position, portions of the spring member are medially biased away from the longitudinal axis of the bore toward the outer wall of upper region of the bore, which increases the effective inner diameter of the upper region of the bore, the bone screw removal system comprising:

a tubular sleeve member having at least one tongue member formed in a distal end of the sleeve member and defining a conduit extending from the distal end to a proximal end of the sleeve member, wherein the at least one tongue member is resiliently biased inward toward a center of the conduit of the sleeve member, and wherein the conduit of the sleeve member has a first diameter; and a bone screw drive member having a distal end and a proximal end, wherein at least a portion of an exterior surface of the bone screw drive member proximate the distal end of the bone screw drive member has a diameter that is substantially the same as the first diameter of the sleeve member and is configured for slideably receipt therein the conduit of the sleeve member, wherein the at least one tongue member is movable about and between a first, relaxed position, in which the tongue member is resiliently biased inward toward the center of the conduit of the sleeve member, and a second position, in which the at least a portion of the exterior surface of the bone screw drive member proximate the distal end of the bone screw drive member acts against an inner surface of the at least one tongue member to urge the at least one tongue member outwardly away from the center of the conduit of the sleeve member.

2. The bone screw removal system of claim 1, wherein the at least one tongue member comprises a pair of tongue members.

3. The bone screw removal system of claim 1, wherein the at least one tongue member comprises a plurality of tongue members.

4. The bone screw removal system of claim 1, wherein the at least one tongue member is equal to the number of spring members of the bone screw retaining system.

5. The bone screw removal system of claim 1, wherein a portion of the distal end of the bone screw driver is configured to operatively engage a head of the bone screw.

6. The bone screw removal system of claim 5, wherein a portion of the distal end of the bone screw driver is configured to seat therein a bore of the plate, and wherein the at least one tongue member is positioned in opposition to the spring member.

7. The bone screw removal system of claim 6, wherein the first diameter of the conduit of the sleeve member is greater than the diameter of the head of the bone screw.

8. The bone screw removal system of claim 1, wherein a portion of the proximal end of the bone screw drive member forms a handle.

9. The bone screw removal system of claim 1, wherein the conduit of the sleeve member is slideably mountable to bone screw drive member such that the sleeve member can be moved axially about a longitudinal axis of the bone screw drive member.

10. A bone screw removal system for removing bone screws from a plate that defines a plurality of transversely extending bores and a plurality of cavities and a bone screw retaining system that includes an elastically deformable spring member positioned therein each cavity such that portions of the spring member can extend into a portion of the upper region of each of the bores, wherein the spring member is configured to mount therein the cavity and is movable between a first relaxed position and a second compressed position, wherein, in the first relaxed position, at least a portion of the spring member extends outwardly substantially transverse to the longitudinal axis of the bore and into the upper region of the bore, wherein, in the first relaxed position, portions of the spring member extend over portions of the upper region of each bore of the pair of opposing bores, which decreases the effective inner diameter of the upper region of the bore, and wherein, in the second compressed position, portions of the spring member are medially biased away from the longitudinal axis of the bore toward the outer wall of upper region of the bore, which increases the effective inner diameter of the upper region of the bore, the bone screw removal system comprising:

a tubular sleeve member having at least one tongue member formed in a distal end of the sleeve member and defining a conduit extending from the distal end to a proximal end of the sleeve member, wherein the at least one tongue member is resiliently biased inward toward a center of the conduit of the sleeve member; and a bone screw drive member having a distal end and a proximal end, wherein at least a portion of an exterior surface of the bone screw drive member proximate the distal end of the bone screw drive member is configured for slideably receipt therein the conduit of the sleeve member, wherein the at least one tongue member is movable about and between a first, relaxed position, in which the tongue member is resiliently biased inward toward the center of the conduit of the sleeve member, and a second position, in which the at least a portion of the exterior surface of the bone screw drive member proximate the distal end of the bone screw drive member acts against an inner surface of the at least one tongue member to urge the at least one tongue member outwardly away from the center of the conduit of the sleeve member and toward a peripheral edge of the distal end of the sleeve member.

11. The bone screw removal system of claim 10, wherein the conduit of the sleeve member has a first diameter, and wherein the exterior surface of the bone screw drive member proximate the distal end of the bone screw drive member has a diameter that is substantially the same as the first diameter of the sleeve member.

12. The bone screw removal system of claim 10, wherein the at least one tongue member comprises a pair of tongue members.

13. The bone screw removal system of claim 10, wherein the at least one tongue member comprises a plurality of tongue members.

14. The bone screw removal system of claim 10, wherein the at least one tongue member is equal to the number of spring members of the bone screw retaining system.

15. The bone screw removal system of claim 10, wherein a portion of the distal end of the bone screw driver is configured to operatively engage a head of the bone screw.

16. The bone screw removal system of claim 15, wherein a portion of the distal end of the bone screw driver is configured to seat therein a bore of the plate, and wherein the at least one tongue member is positioned in opposition to the spring member.

17. The bone screw removal system of claim 16, wherein the first diameter of the conduit of the sleeve member is greater than the diameter of the head of the bone screw.

18. The bone screw removal system of claim 10, wherein a portion of the proximal end of the bone screw drive member forms a handle.

19. The bone screw removal system of claim 10, wherein the conduit of the sleeve member is slideably mountable to bone screw drive member such that the sleeve member can be moved axially about a longitudinal axis of the bone screw drive member.

* * * * *